United States Patent
Lo

(10) Patent No.: US 6,468,246 B1
(45) Date of Patent: Oct. 22, 2002

(54) NEEDLE HOLDER MOUNTING ARRANGEMENT FOR SAFETY HYPODERMIC SYRINGE

(75) Inventor: Cheng-Chi Lo, Yungho (TW)

(73) Assignee: M.K. Meditech Co., Ltd., Taoyuan (TW)

( * ) Notice: Subject to any disclaimer, the term of this patent is extended or adjusted under 35 U.S.C. 154(b) by 0 days.

(21) Appl. No.: 09/993,478

(22) Filed: Nov. 27, 2001

(51) Int. Cl.7 ................................................ A61M 5/00
(52) U.S. Cl. ...................................... 604/110; 604/195
(58) Field of Search .......................... 604/10, 187, 181, 604/192, 195, 197–198, 218, 263, 240–242; 128/919

(56) References Cited

U.S. PATENT DOCUMENTS 5,634,903 A * 6/1997 Kurose et al. .............. 604/110
5,693,023 A * 12/1997 Adams ....................... 604/110
5,820,605 A * 10/1998 Zdeb et al. ................. 604/110
6,193,687 B1 * 2/2001 Lo .............................. 604/110

* cited by examiner

Primary Examiner—Manuel Mendez
Assistant Examiner—Michael M Thompson
(74) Attorney, Agent, or Firm—Bacon & Thomas, PLLC

(57) ABSTRACT

A needle holder mounting arrangement for safety hypodermic syringe is disclosed, which includes a barrel, a needle holder, and an expansion ring. The barrel has an annular locating groove extended around the inside wall of the front small inner diameter section thereof. The needle holder has a front coupling section and a rear positioning section received in a front small inner diameter section of the barrel, the side openings, and the movable positioning blocks respectively connected to the inside wall thereof by a respective springy connecting strip. The positioning blocks are engaged with the locating groove of the barrel to stop the needle holder from backward movement accidentally after installation of the expansion ring in the needle holder.

4 Claims, 6 Drawing Sheets

NEEDLE HOLDER MOUNTING ARRANGEMENT FOR SAFETY HYPODERMIC SYRINGE

BACKGROUND OF THE INVENTION

1. Field of the Invention

The present invention relates to a safety hypodermic syringe and, more particularly, to a needle holder mounting arrangement for safety hypodermic syringe.

2. Description of Related Art

In a safety hypodermic syringe, the plunger has an arrowhead-like front tip adapted for hooking the needle holder, for enabling the needle holder and the needle cannula at the needle holder to be pulled backwards to the inside of the barrel to prevent contamination after the service of the safety hypodermic syringe. The needle holder is press-fitted into the inside of the front section of the barrel. However, when installing the needle cannula in the needle holder, the backward pressure from the needle cannula tends to force the needle holder out of position. Further, in order to prohibit the needle holder from escaping out of the barrel from the front side of the barrel, the barrel is made having a conical front end. This conical front end design prohibits the needle holder from forward movement relative to the barrel, however it facilitates backward movement of the needle holder in the barrel during installation of the needle cannula in the needle holder. In order to ensure positive positioning of the needle holder in the barrel, the friction-fit between the needle holder and the inside wall of the barrel is enhanced. However, enhancing the friction-fit between the needle holder and the inside wall of the barrel complicates the installation of the needle holder in the barrel. Further, an injection molding mold for molding needle holders or barrels for safety hypodermic syringe has multiple cavities. Because the injection environment (fluid material filling position, injection temperature, cooling speed, etc.) in each cavity is different, it is difficult to control the dimensions of the injection-molded finished products precisely. A small specification tolerance may cause the needle holder and the barrel unable to match each other perfectly.

Therefore, it is desirable to provide a needle holder mounting arrangement for safety hypodermic syringe that eliminates the aforesaid problems.

SUMMARY OF THE INVENTION

The main object of the present invention is to provide a needle holder mounting arrangement for safety hypodermic syringe, which prevents backward movement of the needle holder to the inside of the barrel accidentally. It is another object of the present invention to provide a needle holder mounting arrangement for safety hypodermic syringe, which is easy and inexpensive to manufacture.

To achieve these and other objects of the present invention, the needle holder mounting arrangement for safety hypodermic syringe comprises a barrel, a needle holder, and an expansion ring. The barrel comprises a fluid chamber. The fluid chamber has a front small inner diameter section, a rear big inner diameter section, and at least one locating means, for example, an inside annular locating groove in the inside wall of the front small inner diameter section. The needle holder comprises a front coupling section and a rear positioning section received in the front small inner diameter section of the barrel, a longitudinal center through hole axially extended through the front coupling section and the rear positioning section. The longitudinal center through hole has a rear receiving open chamber. The rear positioning section comprises at least one, for example, two side openings symmetrically disposed in the periphery thereof at two sides corresponding to the locating means, a plurality of movable positioning blocks respectively suspended in the side openings and partially projecting into the rear receiving open chamber of the longitudinal center through hole, and a plurality of springy connecting strip respectively connected between the rear end of the movable positioning blocks and the inside wall of the side openings. Each movable positioning block has a front inner hooked portion, and an outer protruded engagement portion adapted for engaging the locating means of the barrel. The expansion ring is press-fitted into the rear receiving open chamber of the needle holder to force the outer protruded engagement portion of each movable positioning block expanded outwards and engaged into the locating means of the barrel after insertion of the expansion ring into the rear receiving open chamber of the needle holder, stopping the needle holder from backward movement relative to the barrel accidentally. The expansion ring has a longitudinally extended center through hole, which is disposed in fluid communication with the longitudinal center through hole of the needle barrel.

After injection, the plunger of the safety hypodermic syringe is pushed forwards further to move the expansion ring to the front end of the rear receiving open chamber of the needle holder, for enabling the springy connecting strips to turn the movable positioning blocks inwards from the locating groove of the barrel and to force the positioning blocks into engagement with the arrowhead-like front retaining tip of the plunger so that the needle holder with the attached needle cannula are pulled backwards with the plunger and received inside the barrel upon back stroke of the plunger.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
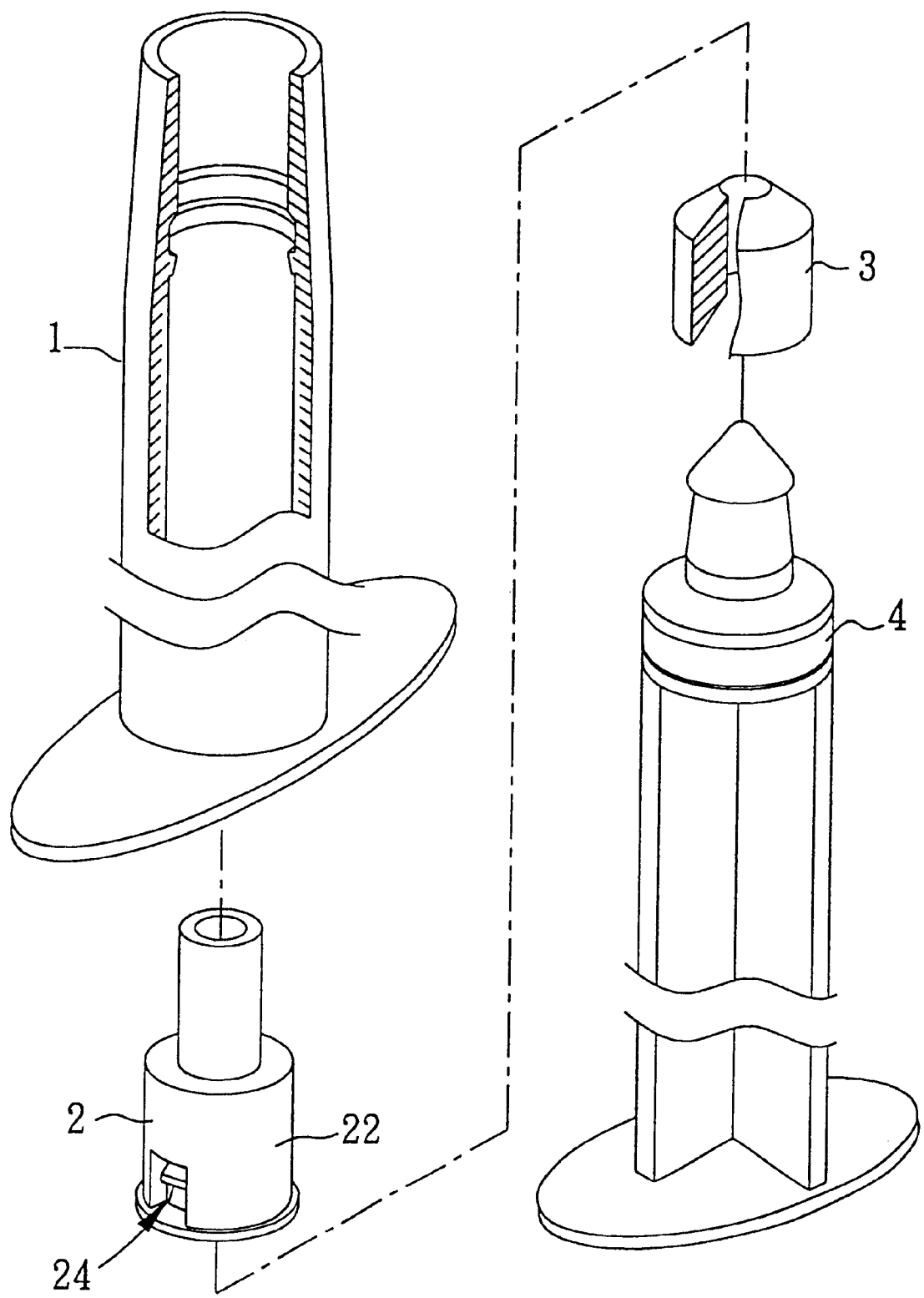
FIG. 1 is an exploded view of the preferred embodiment of the present invention.

With reference to FIG. 1, a needle holder mounting arrangement for safety hypodermic syringe is shown comprised of a barrel 1, a needle holder 2, an expansion ring 3, and a plunger 4.

Figure 2:
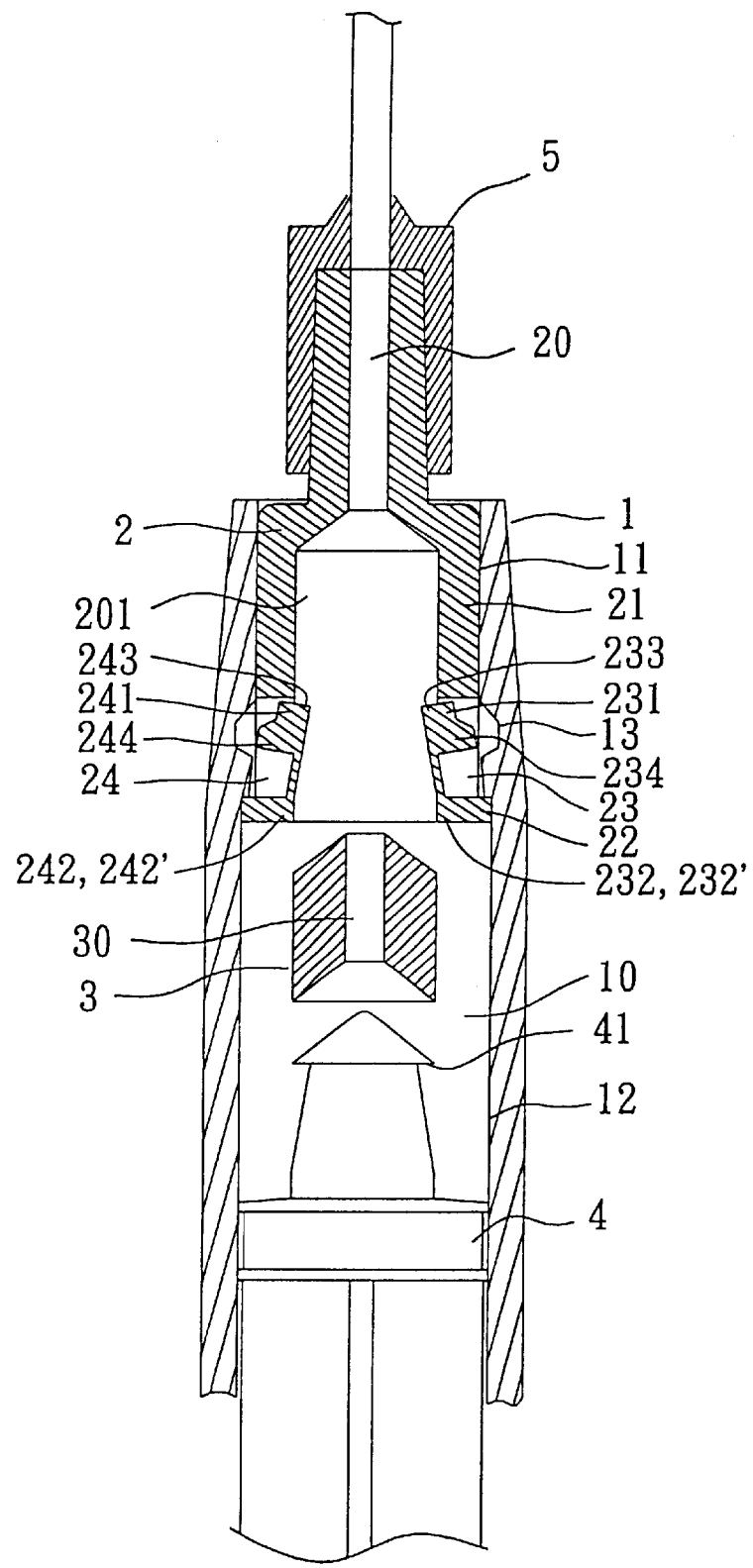
FIG. 2 is a sectional view of the preferred embodiment of the present invention before the connection of the expansion ring to the needle holder.

Referring to FIG. 2 and FIG. 1 again, the barrel 1 is a hollow cylindrical member comprising a fluid chamber 10.

The fluid chamber 10 has a front small inner diameter section 11, a rear big inner diameter section 12, and a locating groove 13 disposed in the front small inner diameter section 11. According to the present preferred embodiment, the locating groove 13 is an endless groove extended around the inner surface of the front small inner diameter section 11.

Referring to FIGS. 1 and 2 again, the needle holder 2 is adapted for holding a needle cannula 5 in the front side of the barrel 1, comprising a front coupling section 21, a rear positioning section 22, a longitudinal center through hole 20 axially extended through the front coupling section 21 and the rear positioning section 22. The longitudinal center through hole 20 has a rear receiving open chamber 201. The front coupling section 21 and the rear positioning section 22 are received in the front small inner diameter section 11 of the barrel 1. The rear positioning section 22 comprises two side openings 23 and 24 symmetrically disposed in the periphery thereof at two opposite sides corresponding to the locating groove 13 of the barrel 1, two movable positioning blocks 231 and 241 respectively suspended in the side openings 23 and 24 and partially projecting into the rear receiving open chamber 201 of the longitudinal center through hole 20, two symmetrical pairs of springy connecting strips 232, 232'; 242, 242' respectively connected between the rear end of the movable positioning blocks 231 and 241 and the inside wall of the side openings 23 and 24 (see FIG. 2). The movable positioning blocks 231 and 241 each have a front inner hooked portion 233 or 243, and an outer protruded engagement portion 234 or 244. The expansion ring 3 fits the inner diameter of the rear receiving open chamber 201 of the needle holder 2, having a longitudinally extended center through hole 30 for the passing of fluid medicine.

Figure 3:
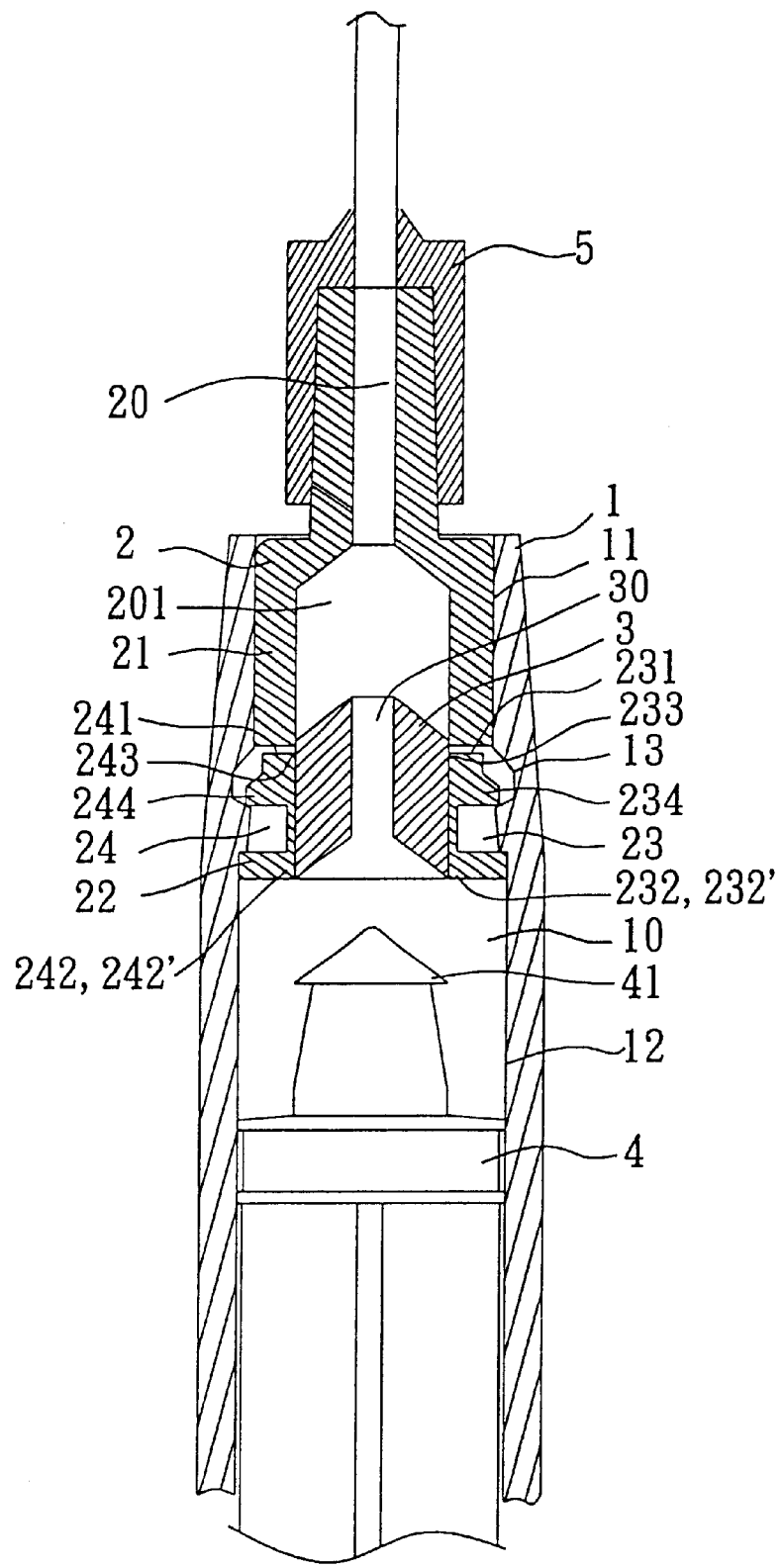
FIG. 3 is a sectional assembly view of the preferred embodiment of the present invention showing the expansion ring fitted into the rear end of the rear receiving open chamber of the needle holder.

The assembly process of the present invention is outlined hereinafter with reference to FIGS. 2 and 3. The needle holder 2 inserted in proper order into the fluid chamber 10 of the barrel 1 from the rear side and forced into friction-engagement with the inner surface of the front small inner diameter section 11 of the barrel 1, and then the expansion ring 3 is put in the barrel 1 and inserted into the rear receiving open chamber 201 of the needle holder 2. At this time, as shown in FIG. 3, the expansion ring 3 is positioned in the inside of the rear positioning section 22 of the needle holder 2, and the center through hole 30 of the expansion ring 3 is disposed in fluid communication with the longitudinal center through hole 20 of the needle holder 2 for the passing of fluid medicine to the needle cannula 5 at the front side of the needle holder 2 out side the barrel 1. Upon insertion of the expansion ring 3 into the rear receiving open chamber 201 of the needle holder 2, the expansion ring 3 forces the movable positioning blocks 231 and 241 radially outwards, thereby causing the movable positioning blocks 231 and 241 to force the respective outer protruded engagement portions 234 and 244 into engagement with the locating groove 13 of the barrel 1, and therefore the needle holder 2 is positively secured in position in the inside of the barrel 1.

Because the outer protruded engagement portions 234 and 244 of the movable positioning blocks 231 and 241 are maintained engaged in the locating groove 13 of the barrel 1, the movable positioning blocks 231 and 241 bear the backward force produced during the installation of the needle cannula 5 in the front side of the needle holder 2, preventing the needle holder 2 from backward movement.

Figure 4:
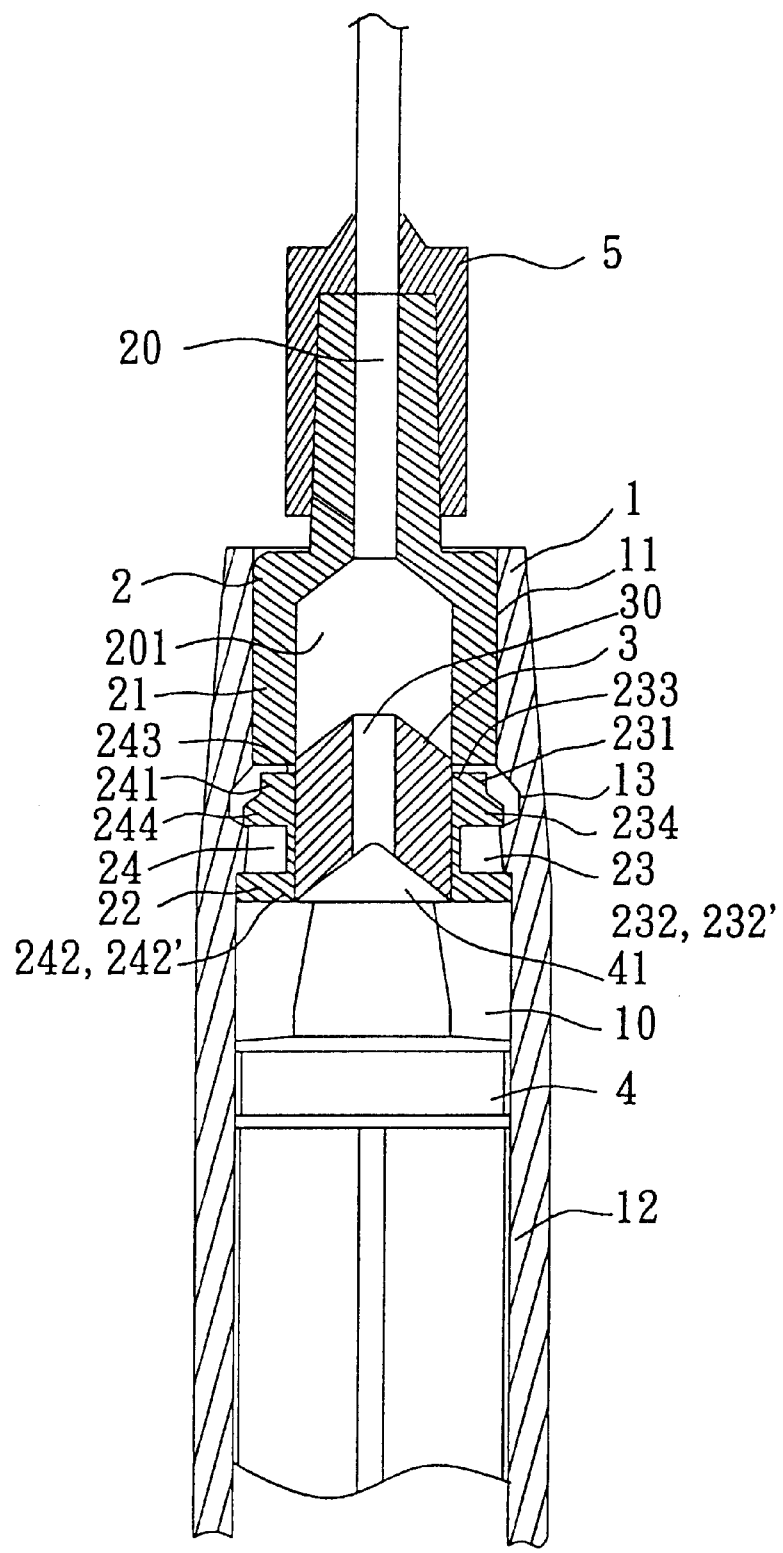
FIG. 4 is a sectional view showing the action of the preferred embodiment of the present invention (I).

Referring to FIG. 4, after injection, the arrowhead-like front retainer tip 41 of the plunger 4 is partially engaged into the rear end of the center through hole 30 of the expansion ring 3.

Figure 5:
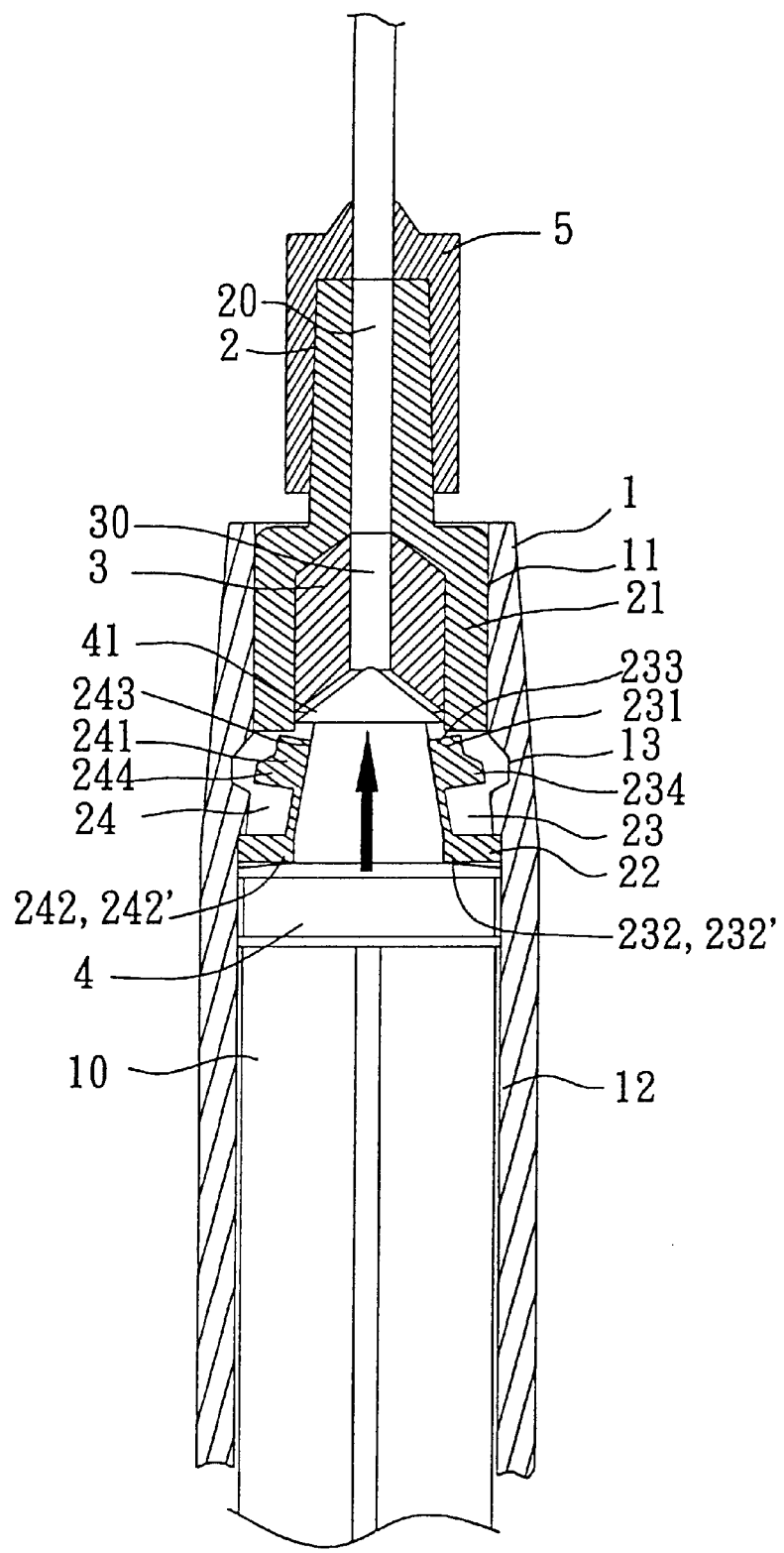
FIG. 5 is a sectional view showing the action of the preferred embodiment of the present invention (II).

Referring to FIG. 5, when continuously pushing the plunger 4 forwards after injection, the expansion ring 3 is completely forced into the inside of the rear receiving open chamber 201 of the needle holder 2 and disposed in front of the movable positioning blocks 231 and 241, i.e., the radially extended outward pressure is released from the movable positioning blocks 231 and 241. At this time, the connecting strips 232, 232'; 242, 242' move the movable positioning blocks 231 and 241 backwards from the locating groove 13 of the barrel 1 due to the effect of the material spring power of the needle holder 2 to such a position where the front inner hooked portions 233 and 243 of the movable positioning blocks 231 and 241 are respectively aimed at the arrowhead-like front retainer tip 41 of the plunger 4.

Figure 6:
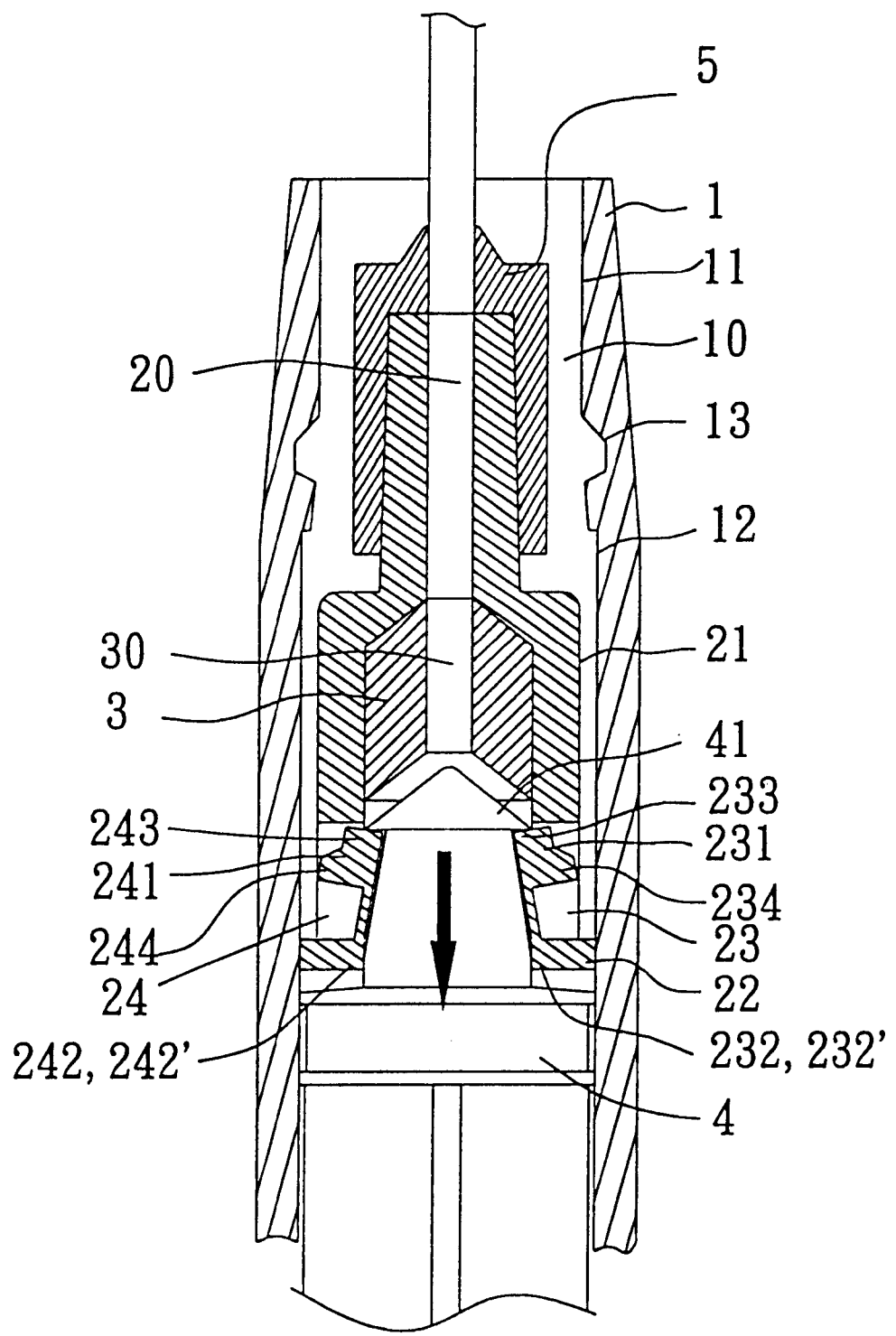
FIG. 6 is a sectional view showing the action of the preferred embodiment of the present invention (III).

Referring to FIG. 6, when pulling the plunger 4 backwards, the arrowhead-like front retainer tip 41 of the plunger 4 is forced into engagement with the front inner hooked portions 233 and 243 of the movable positioning blocks 231 and 241, and therefore continuously pulling the plunger 4 backwards causes the needle holder 2 and the attached needle cannula 5 to be moved backwards with the plunger 4 and received the inside of the barrel 1.

As indicated above, the positive positioning of the needle holder in the barrel does not depend upon friction fitness between the inner diameter of the barrel and the outer diameter of the needle holder. Therefore, the precision requirement for the needle holder and the barrel is less critical, and the needle holder and the barrel can be made by injection molding to reduce the manufacturing cost.

A prototype of needle holder mounting arrangement for safety hypodermic syringe has been constructed with the features of FIGS. 1~6. The safety hypodermic syringe functions smoothly to provide all of the features discussed earlier.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A needle holder mounting arrangement for safety hypodermic syringe comprising:

a barrel, said barrel comprising a fluid chamber, said fluid chamber having a front small inner diameter section, a rear big inner diameter section, and at least one locating means in an inside wall of said front small inner diameter section;

a needle holder mounted in said barrel, said needle holder comprising a front coupling section and a rear positioning section received in the front small inner diameter section of said barrel, a longitudinal center through hole axially extended through said front coupling section and said rear positioning section, said longitudinal center through hole having a rear receiving open chamber, said rear positioning section comprising at least one side opening in the periphery thereof corresponding to said at least one locating means, at least one movable positioning block respectively suspended in each of said at least one side opening and partially projecting into said rear receiving open chamber of said longitudinal center through hole, at least one springy connecting strip respectively connected between a rear end of said at least one movable positioning block and an inside wall of said at least one side opening, said at least one movable positioning block each having a front inner hooked portion, and an outer protruded engagement portion adapted for engaging the at least one locating means of said barrel; and an expansion ring adapted for engaging and sliding into the rear receiving open chamber of said needle holder to force said outer protruded engagement portion of each of the at least one movable positioning block expanded outwards and engaged into said at least one locating means of said barrel after insertion of said expansion ring into the rear receiving open chamber of said needle holder, said expansion ring having a longitudinally extended center through hole, which is disposed in fluid communication with the longitudinal center through hole of said needle barrel.

2. The needle holder mounting arrangement for safety hypodermic syringe as claimed in claim 1, wherein said rear positioning section comprises at least two side openings symmetrically disposed in the periphery thereof.

3. The needle holder mounting arrangement for safety hypodermic syringe as claimed in claim 1, wherein said expansion ring is press-fitted into the inside of said rear positioning section of said needle holder.

4. The needle holder mounting arrangement for safety hypodermic syringe as claimed in claim 1, wherein at least one the locating means of said barrel is an inside annular groove extended around the inside wall of said front small inner diameter section.

\* \* \* \* \*